United States Patent [19]

Cupples et al.

[11] 4,045,507
[45] Aug. 30, 1977

[54] METHOD OF OLIGOMERIZING 1-OLEFINS

[75] Inventors: Barrett L. Cupples, Franklin Township, Allegheny County; William J. Heilman, Allison Park; A. Norman Kresge, Penn Hills Township, Allegheny County, all of Pa.

[73] Assignee: Gulf Research & Development Company, Pittsburgh, Pa.

[21] Appl. No.: 633,671

[22] Filed: Nov. 20, 1975

[51] Int. Cl.² .................................................. C07C 3/18
[52] U.S. Cl. ........................................... 260/683.15 B
[58] Field of Search .......................... 260/683.15 B

[56] References Cited

U.S. PATENT DOCUMENTS

| 2,850,551 | 9/1958 | Carlsmith | 260/683.15 C |
| 3,658,936 | 4/1972 | Erdmann | 260/683.15 C |
| 3,780,128 | 12/1973 | Shubkin | 260/683.15 B |

*Primary Examiner*—C. Davis

[57] ABSTRACT

The trimer to tetramer ratio of an alpha-olefin oligomer is varied over a significant range in a continuous, multi-stage alpha-olefin oligomerization process including a series of at least two flow-through tank reactors by controlling the amount of conversion taking place in each stage. The multi-stage process is used to prepare various poly(l-decene) oligomer mixtures having different oligomer proportions for use as synthetic lubricants.

10 Claims, No Drawings

METHOD OF OLIGOMERIZING 1-OLEFINS

FIELD OF THE INVENTION

This invention relates to the oligomerization of alpha-olefins, such as 1-decene, and more specifically it relates to a multi-stage, continuous process, including at least two tank reactors in series for controlling the ratio of oligomers in the oligomer product.

DESCRIPTION OF THE PRIOR ART

U.S. Pat. No. 3,149,178 describes the preparation of a synthetic lubricant by the batch polymerization of alpha-olefins, including 1-decene, in a reactor using boron trifluoride together with a promoter such as boron trifluoride.decanol complex or acetic acid.boron trifluoride complex to produce dimer, trimer and a residual polymer fraction.

U.S. Pat. No. 3,382,291 describes the preparation of an alpha-olefin oligomer comprising a dimer, trimer and residual fraction for use as a synthetic lubricant by introducing a stream of the 1-olefin, such as 1-decene, saturated with boron trifluoride and a separate stream of a complex of boron trifluoride and a promoter, such as an alcohol, into a reactor for batch reaction. The patent also describes a continuous process in which a product stream is withdrawn from the reactor at the rate of the influent streams.

U.S. Pat. Nos. 3,763,244 and 3,780,128 describe the batch oligomerization of 1-olefins, such as 1-decene, in a reaction vessel using an alcohol or water co-catalyst and boron trifluoride bubbled through the reaction liquid to provide a molar excess of the boron trifluoride in addition to the boron trifluoride that complexes with the co-catalyst. A product mixture of dimer, trimer, tetramer and higher oligomers is described.

SUMMARY OF THE INVENTION

We have discovered in the oligomerization of 1-olefins that the relative proportion of the higher oligomers and the lower oligomers can be optimized for any particular needs over a substantial range. The novel oligomerization process is carried out using boron trifluoride with a complex-forming co-catalyst in a continuous, multi-stage process including a series of two or more tank reactors.

Oligomers of certain 1-olefins, particularly 1-decene and mixtures of 1-decene with 1-octene and/or 1-dodecene are highly useful as base fluids for preparing lubricants, hydraulic fluids, transmission fluids, transformer fluids, and the like, generically described as functional fluids, by the use of appropriate additives. Alpha-olefin oligomers can, in some instances, also be used as functional fluids without the use of property modifying additives. The alpha-olefin oligomers which are useful either directly or with additives as functional fluids generally have a 210° F. (98.9° C.) viscosity within the range of about one centistoke to about 15 centistokes. Each functional fluid product and generally the base fluid from which it is prepared must conform with established viscosity specifications.

The oligomer product prepared by the multi-stage process described herein is a mixture of the dimer, trimer, tetramer and pentamer with minute amounts of higher oligomers sometimes present. The dimer is generally removed for separate use as a functional fluid, particularly use as a transformer fluid, to avoid volatilization loss from functional fluids comprising the higher oligomers. Therefore, the primary oligomer product for general use is a mixture of the trimer, tetramer and pentamer. But since the different viscosity specifications for the broad range of products for which a trimer, tetramer and pentamer mixture can be used varies over a broad range, the relative proportions of trimer, tetramer and pentamer must vary substantially from functional fluid product to product in order to meet these viscosity specifications. In view of the fact that the amount of pentamer resulting from the oligomerization is generally less than about 15 weight percent and is more difficult to quantify and since the amount of tetramer and the amount of pentamer, in general, increases or decreases similarly in different oligomerization runs at different conditions, we have used the trimer to tetramer ratio as a convenient indicator of the trend of changing product composition from run to run.

Generally, the oligomer composition that is obtained from a prior art polymerization procedure is not the composition that is required to meet the viscosity specifications for a desired product. A separation procedure is required to obtain a fraction having the desired trimer to tetramer ratio but the separation also includes a by-product fraction. It would be advantageous to be able to vary the oligomer composition to make an oligomer product, or different oligomer products in different runs, having the desired composition without a by-product fraction.

When two or more separate functional fluid products are desired, these can be obtained as separate fractions from the crude oligomer product, each fraction having its specific trimer to tetramer ratio to provide the required viscosity. However, the relative amounts of the different fractions obtained on separation is determined by the composition of the crude product resulting from the oligomerization. Since the demand for each product fraction will vary over a period of time, it would be most advantageous to be able to vary their relative rate of production by varying the composition of the crude oligomer product and meet, through fractionation of the crude product, the demand for each individual product without undesired by-product.

The preparation of two functional fluid products from a single oligomer product is now described by way of example. A 1-decene oligomer, stripped of monomer, contained 12 percent dimer, 55 percent trimer, 27 percent tetramer and 6 percent pentamer and higher. The oligomer was hydrogenated and separated into a dimer fraction, a hydraulic base fluid fraction having a 210° F. (98.9° C.) viscosity of 3.94 cs. and a motor oil base fluid fraction having a 210° F. (98.9° C.) viscosity of 5.79 cs. The hydraulic base fluid contained 3 percent dimer, 79 percent trimer, 17 percent tetramer and 1 percent pentamer while the motor oil base fluid contained 1 percent dimer, 37 percent trimer, 46 percent tetramer and 16 percent pentamer. The weight ratio of hydraulic base fluid to motor oil base fluid resulting from this separation was about 1.4 to one.

We have discovered a simple, flexible procedure for controlling the ratio of lower to higher oligomers, as indicated by the trimer to tetramer ratio, over a significant range during the oligomerization of alpha-olefins. We have discovered that this variation in the trimer to tetramer ratio can be effected in a continuous, multi-stage procedure in which the 1-olefin and the catalysts are introduced into and mixed together in a tank reactor for partial polymerization to oligomer and then directed to another for partial polymerization to oligomer and then directed to another or more tank reactors in series for further oligomerization. We have discovered that in this procedure the trimer to tetramer ratio is increased by decreasing either or both the overall conversion and the proportion of the total oligomerization taking place in the first reactor and conversely the ratio is decreased by increasing either or both the overall conversion and the proportion of the total oligomerization taking place in the first reactor. Thus, we have discovered as a feature of our invention that the trimer to tetramer ratio is increased at constant conversion by increasing the proportion of the total oligomerization taking place subsequent to the first reactor.

The novel process described herein can be utilized to vary the proportion of lower oligomers and higher oligomers during oligomerization of a broad class of alpha-olefins including those having between about five and about 14-carbon atoms and mixtures thereof. However, since the trimer, tetramer and pentamer are of particular significance in lubricants and other functional fluids, the process is particularly useful in the oligomerization of those alpha-olefins which result in superior functional fluid compositions. For this reason we find that this multi-stage process is more useful in the oligomerization of mixtures of 1-decene with up to 50 mol percent of 1-octene or 1-dodecene or a mixture of these and preferably most useful in the oligomerization of 1-decene itself. The alpha-olefins useful herein are the straight chain compounds as well as the branched chain compounds provided that the branch is on the third or fourth carbon atom or higher.

Boron trifluoride is used as a catalyst in our process together with a compound commonly called a promoter or a co-catalyst. The co-catalyst is conventional and can be any compound which complexes with boron trifluoride to form a coordination compound which is catalytically active for the oligomerization reaction. Included in this list of co-catalysts are aliphatic ethers, such as dimethyl ether, diethyl ether and the like; aliphatic alcohols such as methanol, ethanol, n-butanol, decanol, and the like; polyols, such as ethylene glycol, glycerol and the like; water; aliphatic carboxylic acids such as acetic acid, propanoic acid, butyric acid, and the like; esters, such as ethyl acetate, methyl propionate, and the like; ketones, such as acetone and the like; aldehydes, such as acetaldehyde, benzaldehyde, and the like; acid anhydrides, such as acetic acid anhydride, succinic anhydride, and the like; and the like. It is preferred that the above-described co-catalyst have from one to about 10 carbon atoms although higher carbon co-catalyst compounds can be used. The co-catalyst can be used in a catalytic amount such as from about 0.01 to about 3.0 weight percent of the 1-olefin, preferably from about 0.1 to about 1.0 weight percent. When the amount is low; the reaction becomes slow and when it is too high, there is no added benefit.

The boron trifluoride, introduced into the first reactor, will complex with the co-catalyst. It is preferred that the reaction liquid contain an excess of boron trifluoride in addition to that complexed with the co-catalyst in order to have a suitable rate of oligomerization. We have found that this can be accomplished in a simple manner by pressuring the first reactor with boron trifluoride gas. By this technique sufficient boron trifluoride gas dissolves in the reaction liquid not only to complex with the co-catalyst but also to provide free boron trifluoride in solution. The pressure of boron trifluoride gas that is maintained in the first reactor can suitably range from about 5 to about 500 psig. (0.352 to 35.2 Kg/cm$^2$) or higher with a preferred range of about 20 to about 100 psig. (1.41 to 7.03 Kg/cm$^2$). Alternatively, the boron trifluoride gas can be bubbled through the liquid into the first stage maintained under atmospheric or higher pressure with boron trifluoride gas recycle. Other procedures are known in the art for introducing boron trifluoride into the reaction solution.

The temperature required for suitable oligomerization is conventional and can broadly range from about $-20°$ to about 90° C. with a temperature in the range of about 20° to about 70° C. being preferred. The higher the temperature the greater the rate of catalyst consumption and the lower the rate of reaction while the lower the temperature, the greater the cooling costs with the reaction rate being satisfactory at the lower temperatures.

The first-stage tank reactor serves several important functions. These include the intimate mixing of the various components, the dissolution of boron trifluoride gas, and the control of the temperature of the reaction liquid during the exothermic oligomerization reaction. In the present process the reactant alpha-olefin and the catalysts are continuously introduced into the first stage tank reactor with reactor liquid being continuously withdrawn at a rate that will maintain a constant liquid level in the first reactor and fed to the second reactor. In order to provide a uniform distribution of the components in the first reactor it is desirable to provide some means to add the various components into the reactor and rapidly disperse them in order to provide a substantially homogeneous reaction medium. This can be conveniently accomplished by providing an externally driven stirrer. Another method involves the agitation of the entire reactor and contents by rocking or vibration, but this method is not particularly suitable with large reactors. Also bubbling boron trifluoride gas into the reactor provides some mixing of the reactor contents.

The expression tank reactor as used herein refers to a reactor in which the major dimensions are similar so that substantial homogeneity of composition and temperature can be maintained in the reaction fluid. Thus, it is preferred that the reactor itself be so dimensioned that the major dimension of the reactor differs from the minor dimension by a factor no greater than about ten to one, for example, height to diameter or vice versa. More preferably, it is desired that the major and minor dimensions of the reactor vary no more than by a factor of about five to one and most desirably by a factor no greater than about two and one-half to one for most effective functioning in accordance with the process herein. It is understood that the reactors will operate at a suitable liquid level for effective functioning thereof with stirring means preferred in each.

The exothermic oligomerization reaction is conveniently controlled in the first reactor by the diluting effect of the reactor liquid on the incoming 1-olefin. If greater dilution for temperature control is desirable, the reactor liquid volume can be increased, the inflow rate can be decreased, or an inert diluent can be added to the reactor with the 1-olefin feed. Temperature control is also desirably accomplished by heat exchange means associated with the first reactor. Various factors which affect the degree of oligomerization taking place in this first stage reactor include the average time which the reaction liquid is in the reactor as measured by the liquid volume in the reactor divided by the flow rate from or into the reactor and the reaction rate, which is itself dependent on such factors as the concentration of the catalyst, the concentration of 1-decene and the temperature.

A stream of reaction liquid is continuously removed from the first reactor and introduced into the second reactor. This reaction liquid contains oligomer, 1-olefin, boron trifluoride complex and boron trifluoride in solution. The oligomerization reaction proceeds further in this second reactor. Preferably the second tank reactor is provided with stirring means to insure homogeneity. If no additional tank reactors are to be used in this series, the degree of total overall conversion can be increased by increasing the ratio of reaction liquid in the second reactor to that in the first reactor. It is preferred in this series reactor arrangement, that the ratio of reactor volume in each downstream tank reactor to that in the first reactor be between about 1:5 and about 10:1, most preferably about 1:2 to about 5:1. When a series of three or more, generally up to a maximum of five or six tank reactors, is used, the reactors can conveniently be substantially identical in design. When only two reactors are used, it may be preferable to use a second tank reactor which is substantially greater in volume than the first reactor to more simply accomplish a greater proportion of the overall reaction in the second reactor. Although the temperature in the reactors can be the same or different, it is most practical to operate the reactors at the same or substantially similar temperature.

We have discovered that the trimer to tetramer ratio decreases with increasing conversion in both reactors but that this decrease is less in the second and succeeding, if any, reactors than in the first reactor. We have also discovered that for any specific conversion that the trimer to tetrame ratio is higher in the second and succeeding, if any, reactors than in the first reactor. Thus, we have discovered that we can control the trimer to tetramer ratio over a substantial range by varying the percent of overall conversion of 1-olefin to oligomer that is accomplished in the first stage. At substantially complete overall conversion, the trimer to tetramer ratio is increased as the percent of conversion in the first reactor is decreased and the conversion in the second and succeeding, if any, reactors is increased. Furthermore, the trimer to tetramer ratio can be further increased at low conversion in the first reactor if the amount of conversion in the second and succeeding, if any, reactors is also reduced. This procedure of less than complete overall conversion is less preferred when substantial unreacted 1-olefin must be separated out and recycled unless the demand for the very high trimer to tetramer ratio warrants this additional expense.

The relative amount of conversion undertaken in the first-stage reactor can be controlled by several techniques used alone or in combination. A convenient way, particularly in a relatively large reactor, is by raising or lowering the liquid level in the first reactor without a substantial change in the flow-through rate. When the reactor liquid level (i.e., volume) is increased at constant inflow, the percent conversion in the tank reactor increases and when it is decreased, the percent conversion decreases. The conversion in the first stage can also be controlled by changing the flow rate through the first reactor at constant liquid volume, the higher the flow rate, the lower the conversion. This technique possesses the potential disadvantage that it changes the flow rate through the succeeding reactors and may affect the overall conversion particularly if the flow rate is increased. The percent conversion in the first reactor can also be controlled by reducing the reaction rate and this can be done by reducing the amount of co-catalyst, and consequently the amount of catalyst complex, below the optimum level. However, this technique may require the addition of co-catalyst to the input of the second reactor for efficient utilization of the equipment.

Another method for reducing the conversion in the first reactor involves the introduction of an inert diluent into the first reactor. The inert diluent preferably is easily separated from the products and unreacted 1-olefin and can suitably be a hydrocarbon such as pentane, hexane, heptane and the like. This inert diluent technique is less preferred in the sense that the diluent must be separated out and it involves a less efficient use of the equipment. On the other hand, as noted above, an inert diluent can desirably help control the reaction temperature in the first stage by its diluting effect. The inert diluent desirably is not used in an amount greater than 80 weight percent of the total reaction liquid and preferably no greater than about 50 weight percent of the total reaction liquid. We are able to carry out the process very effectively with no inert diluent.

In carrying out our process the percent of total conversion carried out in the first reactor can be as low as about 15 percent, however, a conversion of at least about 30 percent is preferred and at least about 40 percent is more preferred for effective mixing and heat dissipation in the first stage. The percent conversion in the first stage can be as high as about 90 percent of the total conversion with a maximum of about 80 percent being preferred for the production of less viscous product at high conversion with still lower conversions accomplished in the first stage in order to increase the trimer to tetramer ratio. When high conversion is desired following the first reactor, two or more reactors may be useful in the second stage. The additional second-stage reactors can be bypassed, if desired, when reduced second stage conversion is desired.

In general, it is preferred to operate the process at substantially complete overall conversion for most efficient operation. However, if very high trimer to tetramer ratios are desired, the overall conversion can be reduced down to as low as 50 percent or lower with unreacted 1-olefin separated and recycled. When possible, it is usually preferred to obtain the desired trimer to tetramer ratio by adjusting the proportion of the overall conversion carried out in the first reactor in accordance with this invention at a relatively high overall conversion.

In general the dimer is substantially removed from the oligomer product in order to avoid vaporization loss from the functional fluid during use. However, in some uses such as those involving low temperatures or a closed system, a substantial amount of the dimer can be left in the final product provided that the product viscosity specification can be met. But since this dimer will affect the product viscosity, the overall trimer to tetramer ratio to be obtained by the present invention must take into consideration the dimer, if any, that will be left in the final product. The minor amount of pentamer and higher oligomer, if any, is, in general, left in the product. Although the pentamer plus fraction generally is less than about 15 weight percent of the total oligomer product, its effect on product viscosity is significant. The pentamer itself comprises the great preponderance of this fraction with a very small quantity of hexamer and possible heptamer being present.

The oligomer product is hydrogenated to stabilize it and protect it from oxidative degradation either before or subsequent to dimer removal, but preferably before dimer removal since the hydrogenated dimer is itself useful. Conventional hydrogenation catalysts such as palladium, platinum, nickel and the like at a suitable elevated temperature and pressure for hydrogenation, all conventional in this field, are satisfactory.

DESCRIPTION OF PREFERRED EMBODIMENTS

EXAMPLES 1-6

A series of experiments were carried out using a stirred tank reactor at different conversions of the 1-decene feed. These results are compared with a series of experiments carried out in a multi-stage process containing two stirred tank reactors in series.

In the first series a reactor having an effective volume of 580 cc. was equipped with an externally-driven bladed stirrer which vigorously agitated the reactor contents. This reactor was equipped with an internal cooling coil. The 1-decene feed contained about two percent non-reactive impurities. A stream of this 1-decene and a second stream of 1-decene containing 0.6 weight percent n-butanol was introduced into the stirred tank reactor to fill about 60 percent of the effective reactor volume. This reactor was pressured with boron trifluoride gas at a constant pressure of 50 psig. (3.52 Kg/cm$^2$). During steady state opeation the temperature in the stirred tank reactor was maintained at 110° F. (43.3° C.). The reaction rate was varied for each experiment by varying the flow rate of the two feed streams at a substantially constant overall liquid feed rate of about 1,300 ± 100 cc. per hour, thereby varying the overall amount of n-butanol introduced into the reactor. The following Table I sets out the results of these experiments showing the product analysis and the respective conversions.

Table I

| Ex. | Conv. | $C_{20}$ | $C_{30}$ | $C_{40}$ | $C_{50}$ | $C_{30}/C_{40}$ |
|---|---|---|---|---|---|---|
| 1 | 52.7 | 24.1 | 58.8 | 14.4 | 2.7 | 4.08 |
| 2 | 57.5 | 19.0 | 56.7 | 18.8 | 5.5 | 3.01 |
| 3 | 60.0 | 14.0 | 59.5 | 21.0 | 5.5 | 2.83 |
| 4 | 76.6 | 16.9 | 49.9 | 34.1 | 9.1 | 1.46 |
| 5 | 83.4 | 5.2 | 42.6 | 41.4 | 10.9 | 1.02 |
| 6 | 90.5 | 3.8 | 35.1 | 48.0 | 13.1 | .73 |

EXAMPLES 7-13

This series of experiments was carried out in two stirred tank reactors with the product stream from the first reactor introduced directly into the second reactor. The first reactor was a one liter reactor with its internal volume filled to one-half with reactor liquid during steady state operation. The second reactor had a volume of 500 cc. which was filled up at steady state operation. A pressure of 50 psi. (3.52 Kg/cm$^2$) of boron trifluoride gas was maintained over the liquid in the first reactor and a temperature of between 120° and 130° F. 48.9 and 54.5° C.) was maintained within the reactor liquid in each reactor. The reaction rate was varied as described in the preceding experiments while a constant overall feed rate of about two liters per hour of 1-decene was fed to the first reactor, providing an average residence time in each reactor of about 15 minutes. The analysis and conversion of the product stream from the second reactor is set out in Table II.

Table II

| Ex. | Conv. | $C_{20}$ | $C_{30}$ | $C_{40}$ | $C_{50}$ | $C_{30}/C_{40}$ |
|---|---|---|---|---|---|---|
| 7 | 57.6 | 28.5 | 55.6 | 14.2 | 1.7 | 3.92 |
| 8 | 70.4 | 20.6 | 56.8 | 17.3 | 5.3 | 3.3 |
| 9 | 78.3 | 16.9 | 56.1 | 21.2 | 5.9 | 2.6 |
| 10 | 83.5 | 11.5 | 54.5 | 27.7 | 6.3 | 2.0 |
| 11 | 88.2 | 9.5 | 54.1 | 30.7 | 5.7 | 1.8 |
| 12 | 96.0 | 5.6 | 39.4 | 45.2 | 9.8 | 0.9 |
| 13 | 98.7 | 3.6 | 31.6 | 51.3 | 13.5 | 0.6 |

It is noted from these experiments, in comparing Examples 2 with 7 and comparing 5 with 10, for example, that at the same overall conversion the trimer to tetramer ratio is substantially higher and the pentamer content substantially lower, both factors serving to decrease product viscosity, in the multi-stage process of this invention. Thereby the present multi-stage reactor combination provides a very useful method of varying the component proportions within the oligomer and thereby the product viscosity, by controlling the percent of conversion taking place in each stage and by controlling the amount of total conversion.

It is to be understood that the above disclosure is by way of specific example and that numerous modifications and variations are available to those of ordinary skill in the art without departing from the true spirit and scope of the invention.

We claim:

1. The continuous process for polymerizing a 1-olefin to an oligomer mixture including trimer and tetramer which comprises continuously introducing a 1-olefin having from about five to about 14 carbon atoms or a mixture thereof into the first of a series of two or more tank reactors in the presence of a catalytic amount of boron trifluoride and a co-catalyst that complexes with boron trifluoride with mixing therein to provide a substantially homogeneous reaction mixture and continuously removing a partially oligomerized product stream from the first of said tank reactors and introducing said product stream into the second of said tank reactors for further conversion of said 1-olefin to oligomer product, said series of tank reactors being maintained at a same or different temperature suitable for the oligomerization reaction.

2. The continuous process for polymerizing a 1-olefin in accordance with claim 1 in which the 1-olefin is 1-decene or a mixture containing 1-decene and up to about 50 mol percent of 1-octene or 1-dodecene or a mixture thereof.

3. The continuous process for polymerizing a 1-olefin in accordance with claim 2 in which the ratio of the percent conversion of 1-olefin to oligomer in the first reactor to the percent conversion of 1-olefin to oligomer in the subsequent reactors is between about 90:10 and about 15:85.

4. The continuous process for polymerizing a 1-olefin in accordance with claim 3 in which said ratio is between about 80:20 and about 30:70.

5. The continuous process for polymerizing a 1-olefin in accordance with claim 2 in which the total combined conversion of 1-olefin to oligomer is between about 50 percent and about 100 percent of the 1-olefin fed to said first reactor.

6. The continuous process for polymerizing a 1-olefin in accordance with claim 2 in which said catalyst is an aliphatic mono-alcohol having from one to about 10 carbon atoms.

7. The continuous process for polymerizing a 1-olefin in accordance with claim 6 in which said first reactor is pressured with boron trifluoride gas.

8. The continuous process for polymerizing a 1-olefin in accordance with claim 2 in which the ratio of the volume of the first reactor to the volume of each succeeding reactor is between about 5:1 and about 1:10.

9. The continuous process for polymerizing a 1-olefin in accordance with claim 2 in which the ratio of the volume of the first reactor to the volume of each succeeding reactor is between about 2:1 and about 1:5.

10. The continuous process for polymerizing 1-decene to an oligomer mixture including trimer and tetramer which comprises continuously introducing 1-decene into a first tank reactor in the presence of a catalytic amount of boron trifluoride complex and free boron trifluoride with mixing therein to provide a substantially homogeneous reacting mixture and continuously removing a partially oligomerized product stream from said first tank reactor and introducing said product stream into a second tank reactor for further reaction at a temperature in both reactors suitable for oligomerization.

* * * * *